US009649512B2

(12) United States Patent
Matheson

(10) Patent No.: US 9,649,512 B2
(45) Date of Patent: May 16, 2017

(54) ONE OR MORE OF *VIGNA MARINA*, *COCOS NUCIFERA* L. OR *TERMINALIA CATAPPA* L. EXTRACTS FOR TREATING WOUNDS, SKIN DISORDERS AND HAIR LOSS

(75) Inventor: Graham Matheson, Cronulla (AU)

(73) Assignee: CIMTECH PTY LIMITED, New South Wales (AU)

( * ) Notice: Subject to any disclaimer, the term of this patent is extended or adjusted under 35 U.S.C. 154(b) by 376 days.

(21) Appl. No.: 13/318,596

(22) PCT Filed: May 4, 2010

(86) PCT No.: PCT/AU2010/000519
§ 371 (c)(1),
(2), (4) Date: Mar. 15, 2012

(87) PCT Pub. No.: WO2010/127396
PCT Pub. Date: Nov. 11, 2010

(65) Prior Publication Data
US 2012/0164246 A1 Jun. 28, 2012

(30) Foreign Application Priority Data

May 4, 2009 (AU) .................................. 2009901952

(51) Int. Cl.
| A61Q 3/00 | (2006.01) |
| A61K 8/97 | (2017.01) |
| A61K 9/00 | (2006.01) |
| A61K 36/185 | (2006.01) |
| A61K 36/48 | (2006.01) |
| A61K 36/889 | (2006.01) |
| A61L 15/40 | (2006.01) |
| A61L 26/00 | (2006.01) |
| A61Q 7/00 | (2006.01) |
| A61Q 19/08 | (2006.01) |
| A61Q 5/00 | (2006.01) |
| A61Q 19/00 | (2006.01) |

(52) U.S. Cl.
CPC .................. *A61Q 3/00* (2013.01); *A61K 8/97* (2013.01); *A61K 9/0014* (2013.01); *A61K 36/185* (2013.01); *A61K 36/48* (2013.01); *A61K 36/889* (2013.01); *A61L 15/40* (2013.01); *A61L 26/0057* (2013.01); *A61Q 5/00* (2013.01); *A61Q 7/00* (2013.01); *A61Q 19/00* (2013.01); *A61Q 19/08* (2013.01)

(58) Field of Classification Search
None
See application file for complete search history.

(56) References Cited

U.S. PATENT DOCUMENTS

| 6,217,876 | B1 * | 4/2001 | Pauly ............................ 424/769 |
| 6,221,346 | B1 * | 4/2001 | Streels ............................ 424/69 |
| 6,465,023 | B2 | 10/2002 | Pauly |
| 6,551,606 | B1 | 4/2003 | Golz-Berner et al. |
| 2001/0002265 | A1 * | 5/2001 | Pauly ............................ 424/774 |
| 2007/0142306 | A1 | 6/2007 | Maurel et al. |
| 2008/0057108 | A1 | 3/2008 | Koyazounda et al. |
| 2008/0199544 | A1 | 8/2008 | Bellman |
| 2011/0282464 | A1 | 11/2011 | Sargeant et al. |
| 2013/0017239 | A1 | 1/2013 | Viladot Petit et al. |

FOREIGN PATENT DOCUMENTS

| CN | 1170580 | | 1/1998 |
| CN | 101961431 | | 11/2011 |
| CN | 102755488 | | 11/2013 |
| EP | 1747786 | | 1/2007 |
| EP | 1797924 | A1 | 6/2007 |
| EP | 1906980 | | 4/2008 |
| EP | 2008661 | | 12/2008 |
| EP | 2618926 | | 7/2013 |
| EP | 2626077 | | 8/2013 |
| IN | 200701577 | * | 8/2007 |
| JP | 2001031552 | A | 2/2001 |
| JP | 2003-501451 | | 1/2003 |
| JP | 2004-091390 | | 3/2004 |
| JP | 2004-238334 | | 8/2004 |
| JP | 2004359732 | A | 12/2004 |
| JP | 2006045157 | A | 2/2006 |
| JP | 2006069954 | A | 3/2006 |
| JP | 2006160666 | | 6/2006 |
| JP | 2008-037763 | | 2/2008 |
| JP | 2009-013128 | | 1/2009 |
| WO | 2007014334 | | 2/2007 |
| WO | WO-2007067347 | A2 | 6/2007 |
| WO | 2012038061 | | 3/2012 |
| WO | 2012072245 | | 6/2012 |

OTHER PUBLICATIONS

"Treatments". Internet Archive date: Sep. 13, 1999 [Retrieved from the Internet on: May 20, 2013]. Retrieved from: <URL: http://web.archive.org/web/19990913002857/http://www.vodou.org/treatmen.htm>.*
"Coconut" definition by Dictionary.com unabridged origin 1605 and Collins English Dictionary (multiple publication dates including 2009). Retrieved from the Internet: <URL: http://dictionary.reference.com/browse/coconut>.*
"How to extract extra virgin coconut oil". Internet Date: Jun. 4, 2007. Retrieved from the Internet on: Mar. 3, 2014. Retrieved from: <URL: http://answers.yahoo.com/question/index?qid=20070604080521AA2PBwb>.*
"Wound" definition by the American Heritage Dictionary of the English Language, Fourth Edition (2000) and Collins English Dictionary (1991). Retrieved from the Internet: <URL: http://www.thefreedictionary.com/wound>.*

(Continued)

*Primary Examiner* — Amy L Clark
(74) *Attorney, Agent, or Firm* — K&L Gates LLP

(57) ABSTRACT

Biologically active extracts of one or more *Vigna marina* (Burm.) Merr., *Cocos nucifera* L., or *Terminalia catappa* L. and compositions one or more of the extracts are described. The invention also provides therapeutic and cosmetic uses of the extracts and compositions, in particular for promoting wound healing and for the treatment of skin disorders.

6 Claims, 14 Drawing Sheets

(56) References Cited

OTHER PUBLICATIONS

Chansue, et al., The in vitro Antibaceterial Activity and Ornalmental Fish Toxicity of the Water Extract of Indian Almond Leaves (Teminalia catappa Linn.), KKU Veterinary Journal, 2008, 18L1:36-45.

Holdsworth, et al., Traditional Medicinal Plants of Rarotonga, Cook Islands, Part II, International Journal of Pharmacology, 1991, 29:1:71-79.

Yazdi, et al., Antibaceterial Activity of Terminalia Catappa Against Bacteria Isolated from Burn Wounds and Comparison with Effects of Selective Antibodies in vitro, International Journal of Infectious Diseases, International Society for Infectious Diseases, 2008, 12:410.

Extended European Search Report issued in EP10771898 on Oct. 23, 2012.

Nov. 5, 2012 Third Party Observation submitted in EP10771898 (published as EP2427202).

Alviano, D.S., Antinocicpetive and free radical scavenging activities of Cocos nucifera L. (Palmae) husk fiber Aqueous extract, J. of Ethnopharmacology, Jun. 2004, vol. 92, No. 2-3, 269-273.

McClatchey, W., The ethnopharmacopoeia of Rotuma, Journal of Ethnopharmacology vol. 50, Issue 3, Mar. 1996, pp. 147-156.

Nagappa, A.N., Anti-diabetic activity of Terminalia catappa Linn Fruits, J. of Ethnopharmacology, 88 (2003), 45-50.

Mohammad Najmul Ghani Khan; Khazaain-al-Advia, vol. III (20th century AD), Nadeem Yunus Printer/Sheikh Mohd Basheer & Sons, Lahore, 1926 AD p. 478, 479, Formulation ID: JA6/446, Formulation Name: Rughan-e-khopra.

Mohammad Najmul Ghani Khan; Khazaain-al-Advia, vol. III (20th century AD), Nadeem Yunus Printer/Sheikh Mohd Basheer & Sons, Lahore, 1926 AD p. 479, Formulation ID: JA6/446H, Formulation Name: Dawa-e-roghan-e-kopra Brae Jild.

Mohammad Najmul Ghani Khan; Khazaain-al-Advia, vol. III (20th century AD), Nadeem Yunus Printer/Sheikh Mohd Basheer & Sons, Lahore, 1926 AD p. 478, Formulation ID: JA6/446A1, Formulation Name: Rughan-e-kopra Barae Harq-o-salaq.

Kaiyadeva; Kaiyadevanighantau—(Pathyapathyavibodhakah) Edited and translated by P.V. Sharma and Guru Prasad Sharma, Chaukhambha Orientalia, Varanasi, Edn. 1st, 1979 p. 53, Formulation ID: RS6/96A, Formulation Name: Narikela Taila.

Kali Dasa; Vaidyamanorama;—with Hindi translation : Central Council for Research in Ayureda & Siddha, Govt. of India, New Delhi, Edn. 2005 [Time of origin 13th century] p. 104, Formulation ID: RS14/441B, Formulation Name: Vranahar Taila.

Mohammad Najmul Ghani Khan; Khazaain-al-Advia, vol. III (20th century AD), Nadeem Yunus Printer/Sheikh Mohd Basheer & Sons, Lahore, 1926 AD p. 390, Formulation ID: JA6/359X, Formulation Name: Raughan-e-kalonji.

Vagabhata; Astnga Hrdaya—(commentary by Arunadutta) edited by Bhisagacarya Harisastri Paradakara vaidya : Chaukhamba Orientalia, Varanasi, edn. 8th, 1998. [Time of origin 5th century] p. 890, Formulation ID: RS23/1712B, Formulation Name: Mukhdusikahara Lepa.

Kali Dasa; Vaidyamanorama;—with Hindi translation : Central Council for Research in Ayurveda & Siddha, Govt. of India, New Delhi, Edn. 2005 [Time of origin 13th century] p. 54, Formulation ID: RS14/222, Formulation Name: Tungadrum Yogah.

Bharata Bhaisajya Ratnakara—Compiled by Naginadasa Chaganalala Saha, Translated by Gopinath Gupta—vol.-V : B. Jain Publishers, New Delhi, Edn. 2nd. Reprint, Aug. 1999. [This book contains back references from 1000 B.C. to 20th century] p. 272, Formulation ID: HG/842, Formulation Name: Snuhyadyamtailam (01).

Japanese Journal of Clinical and Experimental Medicine, vol. 80, No. 10, pp. 73-78 (2003).

Ashcroft et al., "Estrogen accelerates cutaneous wound healing associated with an increase in TGF-$\beta$1 levels," Nature Medicine, vol. 3, No. 11, Nov. 1997, pp. 1209-1215.

Deenik et al., "Nitrogen Mineralization Potential and Nutrient Availability From Five Organic Materials in an Atoll Soil From the Marshall Islands," Soil Science, Jan. 2008, vol. 173, No. 1, pp. 54-68.

Dweck, "Talking Terminalia," Soap Perfumery and Cosmetics, 1994, vol. 67, Issue 10, pp. 63-64.

Kanda, "Prevention of Skin Aging by Estrogen," Journal of Japanese Cosmetic Science Society, vol. 31, No. 4, pp. 318-324 (2007).

Kanda et al., "Regulatory roles of sex hormones in cutaneous biology and immunology," Journal of Dermatological Science (2005) 38, 1-7.

Majeed et al., "Nurturing Health & Wellness with Coconut Water Solids," Euro Cosmetics, Sep. 2007, vol. No. 15, pp. 22-24.

* cited by examiner

3 Days

5 Days

7 Days

10 Days

Figure 3A          Figure 3B
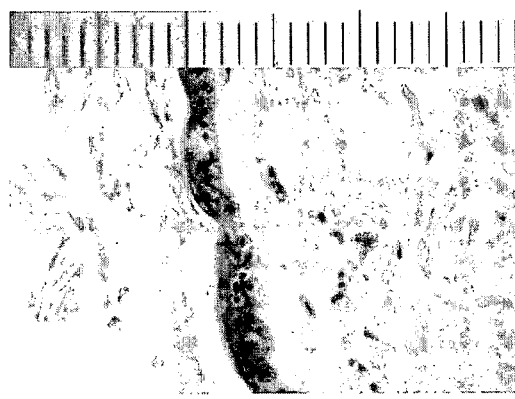 
Figure 3C          Figure 3D
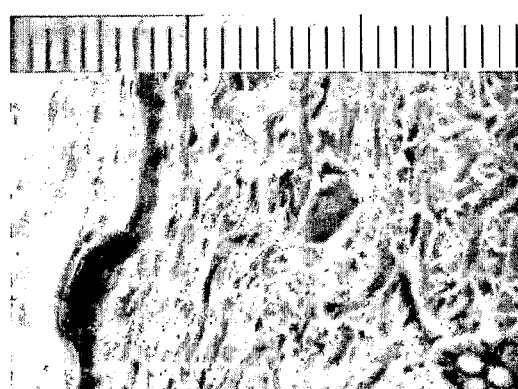 
Figure 3E          Figure 3F

ONE OR MORE OF *VIGNA MARINA*, *COCOS NUCIFERA* L. OR *TERMINALIA CATAPPA* L. EXTRACTS FOR TREATING WOUNDS, SKIN DISORDERS AND HAIR LOSS

This application is a U.S. national phase of International Patent Application No. PCT/AU2010/000519, filed May 4, 2010, which claims the benefit of Australian Patent Application No. 2009901952, filed May 4, 2009.

FIELD OF THE INVENTION

The present invention relates generally to the use of plant extracts and compositions comprising the same for promoting wound healing and for the treatment of skin disorders.

BACKGROUND OF THE INVENTION

The skin has an important role in protection and is the body's first line of defence against disease with the epidermis providing a barrier against microbial invasion. Accordingly, the primary goal in the treatment of wounds, burns, grazes and other damage to the skin is rapid closure and healing of the wound to prevent infection.

Wound healing is a complex process which is generally regarded as involving three overlapping phases: inflammation, proliferation and remodelling. The first phase involves clotting to obtain haemostasis and the recruitment of neutrophils to destroy bacteria and necrotic tissue, followed by recruitment of macrophages. During the second phase angiogenesis occurs in which endothelial cells enter the wound site, simultaneously fibroblasts enter the wound site and help produce granulation tissue. The formation of granulation tissue allows reepithelialisation to take place. During the final remodelling phase the levels of collagen production and degradation equalise and the healed wound is slowly altered to achieve maximal strength. Wound healing is delayed or impaired when any of these processes do not function properly or in a timely manner. This can lead to a chronic wound which can be both a major setback to the individual and a costly clinical problem. Therefore, a composition that speeds up the body's natural process of regenerating dermal and epidermal tissue is advantageous.

The present inventors have surprisingly found that plant extracts disclosed herein and compositions comprising same, promote wound healing and skin repair by inducing early proliferation of the epithelium. Furthermore, these compositions increase the thickness and mechanical strength of the healed wound site. In addition, it has been discovered that these compositions may also provide other therapeutic benefits.

SUMMARY OF THE INVENTION

According to a first aspect of the present invention there is provided a biologically active extract of one or more of *Vigna marina* (Burm.) Merr., *Cocos nucifera* L., or *Terminalia catappa* L.

The extract may further comprise *Hibiscus tiliaceus* L.

In one embodiment the extract is an extract of *Vigna marina* (Burm.) Merr. The extract may be derived from a combination of *Vigna marina* (Burm.) Merr. and *Terminalia catappa* L., a combination of *Vigna marina* (Burm.) Merr. and *Cocos nucifera* L., or a combination of *Vigna marina* (Burm.) Merr., *Cocos nucifera* L., and *Terminalia catappa* L. The extract may be derived from a combination of *Vigna marina* (Burm.) Merr., *Cocos nucifera* L., *Terminalia catappa* L. and *Hibiscus tiliaceus* L.

The extract may be one or more of a leaf, vine, bean, husk or nut extract. Where derived from *Vigna marina* (Burm.) Merr., *Terminalia catappa* L., and *Hibiscus tiliaceus* L., typically the extract is a leaf, vine and/or bean extract. Where derived from *Vigna marina* (Burm.) Merr., typically the extract is a husk and/or nut extract.

The extract may be prepared using, and/or comprise, a plant based oil, a hydrocarbon and/or an alcohol. The plant based oil may be derived from, for example, seeds or fruit. In a particular embodiment the extract is prepared using, and/or comprises, coconut oil. The coconut oil may be virgin coconut oil, refined coconut oil, hydrogenated coconut oil or fractionated coconut oil.

A second aspect of the present invention provides a composition comprising at least one biologically active extract of one or more of *Vigna marina* (Burm.) Merr., *Cocos nucifera* L., or *Terminalia catappa* L., optionally together with one or more pharmaceutically acceptable carriers, diluents or adjuvants. The composition may further an extract derived from *Hibiscus tiliaceus* L.

Typically the composition is applied topically to the skin or to an epidermal appendage of a subject. Epidermal appendages include hair, hair follicles, nails, and cuticles. In one embodiment the composition is used therapeutically and/or cosmetically for the promotion of wound healing or in the treatment of skin disorders. The wound may be a surgical or non-surgical wound. Examples of non-surgical wounds include burns, grazes, cuts and abrasions. Skin disorders include, but are not limited to, age related skin atrophy or steroid related skin atrophy. The age related skin atrophy may be associated with oestrogen deficiency.

In a further embodiment the composition is used for the regeneration of hair. In yet another embodiment the composition is used to increase the thickness and/or mechanical strength of skin and/or an epidermal appendage.

A third aspect of the present invention provides a method for the treatment of wounds and/or for promoting wound healing, the method comprising applying to the skin of a subject a therapeutically effective amount of an extract according to the first aspect or a composition according to the second aspect.

A fourth aspect of the present invention provides method of treating a skin disorder, the method comprising applying to the skin of a subject a therapeutically effective amount of an extract according to the first aspect or a composition according to the second aspect.

A fifth aspect of the present invention provides a method for the regeneration of hair, the method comprising applying to the skin of a subject a therapeutically effective amount of an extract according to the first aspect or a composition according to the second aspect.

A sixth aspect of the invention provides a method for promoting hair growth, the method comprising applying to the skin and/or hair of a subject a therapeutically effective amount of an extract according to the first aspect or a composition according to the second aspect.

A seventh aspect of the present invention provides a method for increasing the thickness and/or mechanical strength of skin and/or an epidermal appendage, the method comprising applying to the skin and/or an epidermal appendage of a subject a therapeutically effective amount of an extract according to the first aspect or a composition according to the second aspect.

An eighth aspect of the present invention provides the use of an extract according to the first aspect for the manufacture of a medicament for the treatment of wounds and/or the promotion of wound healing.

A ninth aspect of the present invention provides the use of an extract according to the first aspect for the manufacture of a medicament for the treatment of a skin disorder.

A tenth aspect of the present invention provides the use of an extract according to the first aspect for the manufacture of a medicament for the regeneration of hair.

An eleventh aspect of the invention provides the use of an extract according to the first aspect for the manufacture of a medicament for promoting hair growth.

A twelfth aspect of the present invention provides the use of an extract according to the first aspect for the manufacture of a medicament for increasing the thickness and/or mechanical strength of skin and/or an epidermal appendage.

BRIEF DESCRIPTION OF THE DRAWINGS

The present invention will now be described, by way of non-limiting example only, with reference to the accompanying drawings in which:

FIG. 2 shows the increase in mechanical wound strength (A) and the average mechanical wound strength (B) for wounds sites of treated animals (test) and untreated animals (control) over the course of 10 days. The treated wounds were subjected to a daily application of a combination extract of *Vigna marina* (Burm.) Merr., *Cocos nucifera* L., *Terminalia catappa* L. and *Hibiscus tiliaceus* L. in coconut oil.

FIG. 3 shows histologic differences in treated (B, D and F) and untreated (A, C and E) skin of 18 month old, oestrogen deficient (ovaries removed at age 6 weeks) rats. The treated skin was subjected to a daily application of a combination extract of *Vigna marina* (Burm.) Merr., *Cocos nucifera* L., *Terminalia catappa* L. and *Hibiscus tiliaceus* L. in coconut oil for 7 days. The skin samples were stained with hematoxylin and eosin and are shown at ×400 magnification.

DETAILED DESCRIPTION OF THE INVENTION

Figures 1A, 1B:
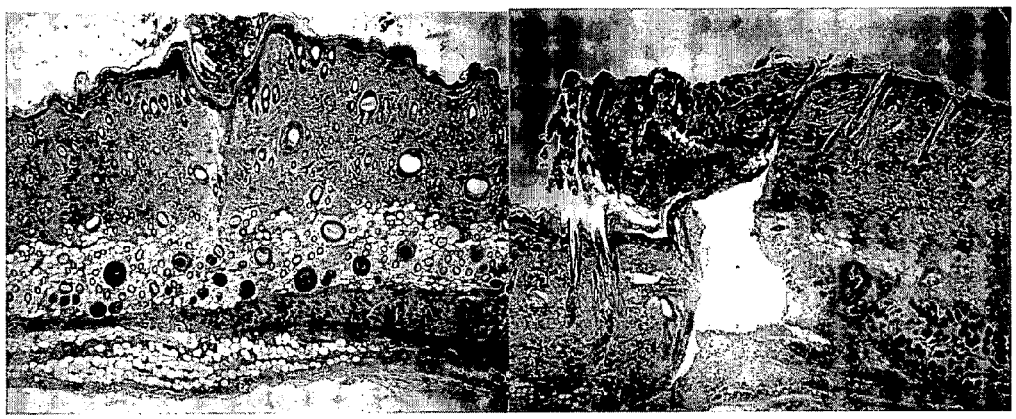
FIG. 1 shows histologic changes in treated (A, C, E and G) and untreated (B, D, F and H) surgically created wound sites on 12 week old healthy female rats at 3, 5, 7 and 10 days post operative. The treated wounds were subjected to a daily application of a combination extract of *Vigna marina* (Burm.) Merr., *Cocos nucifera* L., *Terminalia catappa* L. and *Hibiscus tiliaceus* L. in coconut oil. The skin samples were stained with hematoxylin and eosin and are shown at ×400 magnification.
Figures 1C, 1D:
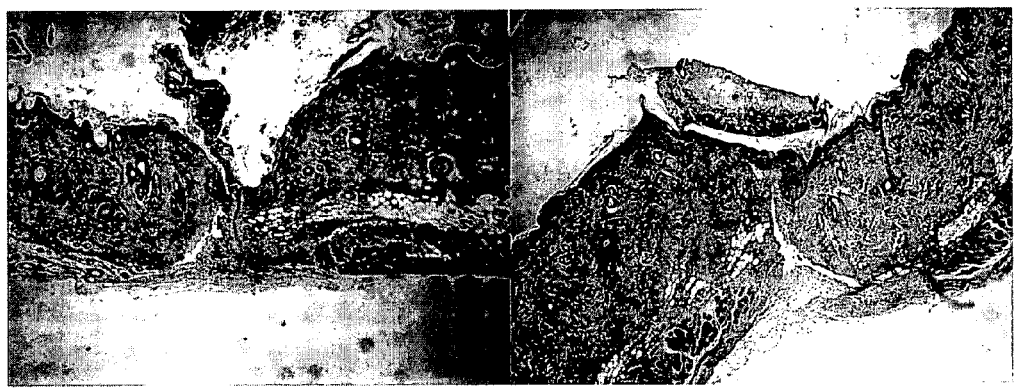
Figures 1E, 1F:
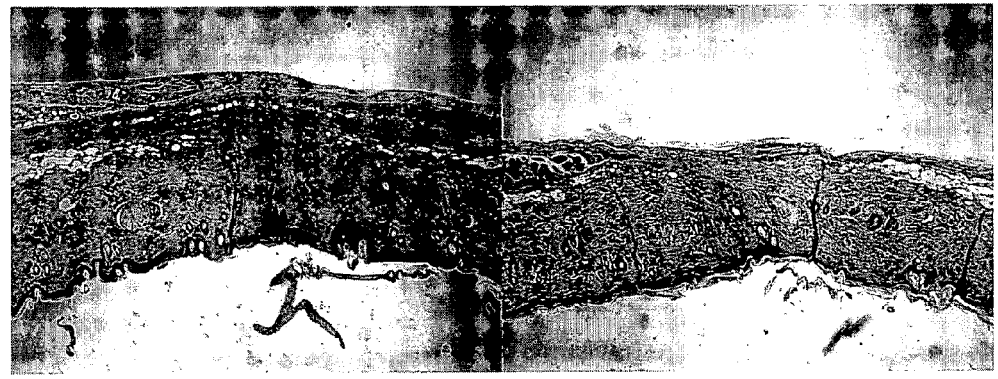
Figures 1G, 1H:
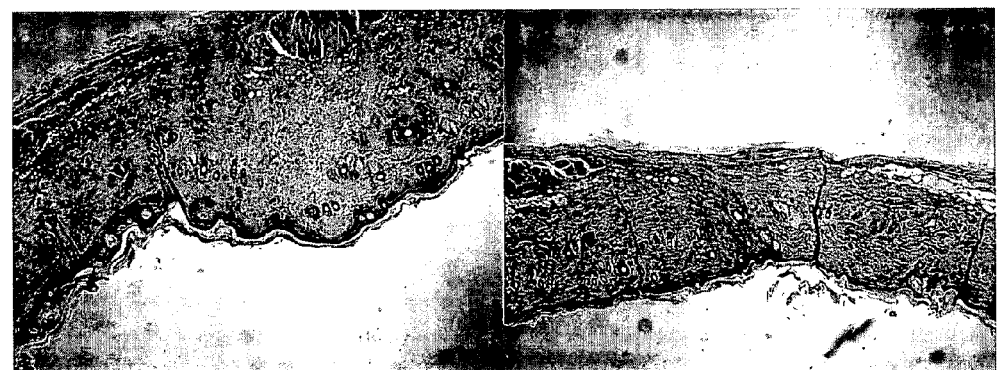

The articles "a" and "an" are used herein to refer to one or to more than one (i.e., to at least one) of the grammatical object of the article. By way of example, "an element" means one element or more than one element.

Throughout this specification and the claims which follow, unless the context requires otherwise, the word "comprise", and variations such as "comprises" or "comprising", will be understood to imply the inclusion of a stated integer or step or group of integers or steps but not the exclusion of any other integer or step or, group of integers or steps.

As used herein the term "extract" refers to an active preparation derived from one or more plants. In the context of the specification by "active" it is meant that the extract is capable of producing a desired therapeutic or cosmetic benefit as disclosed herein. An extract is obtained by a process of "extraction" which will be understood by those skilled in the art as, in general terms, comprising treating plant material with a solvent, a liquid, or a supercritical fluid to dissolve the active preparation and separate the same from residual unwanted plant material. An extract may be in liquid form (for example as a decoction, solution, infusion or tincture) or solid form (for example as a powder or granules). The term "combination extract" as used herein refers to an extract prepared from more than one plant species. In a combination extract the plant material from each of the plant species may be subjected to the extraction process together or separately. That is, material from some or all of the species may be combined prior to addition of the solvent, liquid or supercritical fluid, and/or material from some or all of the species may be independently treated with a solvent, liquid or supercritical fluid and the preparations so obtained are subsequently combined. As such, the same or different solvents (or liquids or supercritical fluids) may be used to extract the active preparation from the different species. The terms "extract" and "combination extract" may be used interchangeably throughout the specification.

The terms "promoting", "promotion" and variations thereof as used herein in the context of wound healing refer to the ability of an extract or composition of the invention to enhance or increase the rate or degree of action of natural physiological process(es) involved in wound healing and the ability of an extract or composition of the invention to enhance or increase the rate of hair growth.

As used herein the terms "treating", "treatment", "preventing" and "prevention" refer to any and all uses which remedy a condition or symptoms, prevent the establishment of a condition or disease, or otherwise prevent, hinder, retard, or reverse the progression of a condition or disease or other undesirable symptoms in any way whatsoever. Thus the terms "treating" and "preventing" and the like are to be considered in their broadest context. For example, treatment does not necessarily imply that a patient is treated until total recovery.

As used herein the terms "effective amount" and "effective dose" include within their meaning a non-toxic but sufficient amount or dose of an agent or compound to provide the desired effect. The exact amount or dose required will vary from subject to subject depending on factors such as the species being treated, the age and general condition of the subject, the severity of the condition being treated, the particular agent being administered and the mode of administration and so forth. Thus, it is not possible to specify an exact "effective amount" or "effective dose". However, for any given case, an appropriate "effective amount" or "effective dose" may be determined by one of ordinary skill in the art using only routine experimentation.

As used herein the term "subject" includes humans, primates, livestock animals (eg. sheep, pigs, cattle, horses, donkeys), laboratory test animals (eg. mice, rabbits, rats, guinea pigs), companion animals (eg. dogs, cats) and captive wild animals (eg. foxes, kangaroos, deer). Typically, the subject is human or a laboratory test animal. Even more typically, the subject is a human.

The present invention is predicated on the inventors' surprising finding, as exemplified herein, that the use of extracts of various plants from Pacific islands possess biological activity when administered to mammalian skin, promoting wound healing and skin repair, increasing epithelial thickness and increasing the mechanical strength of skin. Without wishing to be bound by theory, it is suggested that these biological activities result from the extracts, either directly or indirectly, inducing early proliferation of the epithelium.

Accordingly, one aspect of the present invention provides a biologically active extract of *Vigna marina* (Burm.) Merr., *Cocos nucifera* L., *Terminalia catappa* L. and/or *Hibiscus tiliaceus* L.

The inventors have surprisingly found that extract(s) of *Vigna marina* (Burm.) Merr., *Cocos nucifera* L., *Terminalia catappa* L. and/or *Hibiscus tiliaceus* L alone or in various combination promote the body's natural process of regenerating dermal and epidermal tissue.

Accordingly, extracts of *Vigna marina* (Burm.) Merr., *Cocos nucifera* L., *Terminalia catappa* L. and/or *Hibiscus tiliaceus* L, and compositions containing same are useful therapeutically and/or cosmetically in the promotion of wound healing or in the treatment of skin disorders in a subject. The wound may be a surgical or non-surgical wound. Examples of non-surgical wounds include cuts, burns, grazes, and abrasions. Extracts of the invention may be used in the post-surgical promotion of healing of surgically induced wounds. Skin disorders that may be treated in accordance with embodiments of the invention include but are not limited to age related skin atrophy or steroid related skin atrophy. Age related skin atrophy may be associated with oestrogen deficiency.

It will be appreciated by those skilled in the art that extracts and compositions of the invention also find application in any circumstance in which it is desirable to promote the generation or regeneration of dermal or epidermal tissue or an epidermal appendage. For the purposes of the present invention epidermal appendages include, but are not limited to, hair, hair follicles, nails, and cuticles. By way of example, extracts and compositions of the invention may be used to promote the regeneration of hair follicles, hair and nails. Extracts and compositions of the invention may also be used to increase the thickness and/or mechanical strength of skin and/or an epidermal appendage.

Extracts of the invention may be aqueous, oil and/or organic solvent based extracts, obtained by single, combined and/or successive extraction of any available plant material such as leaves, roots, bark, fruits, shoots, nuts, seeds, flowers and/or wood. Suitable extraction processes, and suitable solvents and liquids for extraction are known to those skilled in the art. Aqueous solvents (for example water, acids, bases); oils (for example coconut); and organic solvents, which can be polar (such as alcohols for example ethanol), non-polar (for example hexane) and/or halogenated (for example dichloromethane), used for extraction can either be used sequentially for extraction or in combination mixture. Importantly, as exemplified herein, the activity of the extract is maintained when extracted into coconut oil, polar solvents (e.g. ethanol) or non-polar solvents (e.g. isopentane). Supercritical fluid extraction using, for example, supercritical nitrogen or carbon dioxide, may also be used in accordance with the invention to obtain extracts.

Further, it will be appreciated by those skilled in the art that an extract of the invention may be subjected to one or more post extraction steps to, for example, increase or maintain the stability of the extract, modify or change the physical form of the extract or assist in formulating the extract into a composition for administration to a subject. By way of example only a liquid form extract may be lyophilised to produce a solid form of the extract.

Extracts of the present invention may be derived from any suitable plant material. Suitable plant material includes leaves, roots, bark, fruits, shoots, nuts, seeds, flowers or wood. The plant material may be, for example, fresh, dried or freeze dried. For any given plant species more than one plant material may be used for the production of extracts. Where derived from *Vigna marina* (Burm.) Merr., *Terminalia catappa* L., and *Hibiscus tiliaceus* L., typically the extract is a leaf, vine and/or bean extract. Where derived from *Vigna marina* (Burm.) Merr., typically the extract is a fresh husk and/or nut extract.

Extract(s) of the invention may be administered in accordance with the present invention in the form of pharmaceutical compositions, which compositions may comprise one or more pharmaceutically acceptable carriers, excipients or diluents. Extracts may further be combined with other therapeutic or cosmetic agents for example, but not limited to, antibiotics, antimicrobial agents, antiseptics, anaesthetics, moisturisers or cosmetic bases. Such compositions may be administered in any convenient or suitable route such as by parenteral, oral, nasal or topical routes. Typically for the purposes of achieving the therapeutic and cosmetic benefits as disclosed herein, the route of administration may be topical. Alternatively, administration by injection, for example subcutaneous injection, may also be appropriate depending on the desired outcome.

It will be understood that the specific dose level of a composition of the invention for any particular individual will depend upon a variety of factors including, for example, the activity of the specific extract(s) employed, the age, body weight, general health and diet of the individual to be treated, the time of administration, the stability of the extract(s), the site of application on the body, and combination with any other treatment or therapy. Single or multiple administrations can be carried out with dose levels and pattern being determined as required depending on the circumstances and the individual to be treated. Suitable dosage regimes can readily be determined by the skilled addressee. A broad range of doses may be applicable. Considering a human subject, for example, from about 0.1 mg to about 1 mg of extract may be administered per kilogram of body weight per day. Dosage regimens may be adjusted to provide the optimum therapeutic response. For example, several divided doses may be administered hourly, daily, weekly, monthly or at other suitable time intervals or the dose may be proportionally reduced as indicated by the exigencies of the situation.

Generally, an effective dosage is expected to be in the range of about 0.0001 mg to about 1000 mg per kg body weight per 24 hours; typically, about 0.001 mg to about 750 mg per kg body weight per 24 hours; about 0.01 mg to about 500 mg per kg body weight per 24 hours; about 0.1 mg to about 500 mg per kg body weight per 24 hours; about 0.1 mg to about 250 mg per kg body weight per 24 hours; about 1.0 mg to about 250 mg per kg body weight per 24 hours. More typically, an effective dose range is expected to be in the range about 1.0 mg to about 200 mg per kg body weight per 24 hours; about 1.0 mg to about 100 mg per kg body weight per 24 hours; about 1.0 mg to about 50 mg per kg body weight per 24 hours; about 1.0 mg to about 25 mg per kg body weight per 24 hours; about 5.0 mg to about 50 mg per kg body weight per 24 hours; about 5.0 mg to about 20 mg per kg body weight per 24 hours; about 5.0 mg to about 15 mg per kg body weight per 24 hours.

Topical formulations typically comprise one or more extracts of the invention together with one or more acceptable carriers, and optionally any other therapeutic ingredients. Formulations suitable for topical administration may be in any suitable form, formulated for example as liminents, lotions, creams, gels, ointments or pastes. Examples of pharmaceutically acceptable carriers or diluents are demineralised or distilled water; saline solution; vegetable based oils such as peanut oil, safflower oil, olive oil, cottonseed oil, maize oil, sesame oil, arachis oil or coconut oil; silicone oils, including polysiloxanes, such as methyl polysiloxane, phenyl polysiloxane and methylphenyl polysolpoxane; volatile silicones; mineral oils such as liquid paraffin, soft paraffin or squalane; cellulose derivatives such as methyl cellulose, ethyl cellulose, carboxymethylcellulose, sodium carboxymethylcellulose or hydroxypropylmethylcellulose; lower alkanols, for example ethanol or isopropanol; lower aralkanols; lower polyalkylene glycols or lower alkylene glycols, for example polyethylene glycol, polypropylene glycol, ethylene glycol, propylene glycol, 1,3-butylene glycol or glycerin; fatty acid esters such as isopropyl palmitate, isopropyl myristate or ethyl oleate; polyvinylpyrridone; agar; carrageenan; gum tragacanth or gum acacia, and petroleum jelly. Typically, the carrier or carriers will form from 10% to 99.9% by weight of the compositions.

Lotions according to the present invention include those suitable for application to the skin or to an epidermal appendage. Lotions or liniments for application to the skin may also include an agent to hasten drying and to cool the skin, such as an alcohol or acetone, and/or a moisturiser such as glycerol, or oil such as coconut oil, castor oil or arachis oil.

Creams, ointments or pastes according to the present invention are semi-solid formulations of the extract for external application. They may be made by mixing the extract in finely-divided or powdered form, alone or in solution or suspension in an aqueous or non-aqueous fluid, with a greasy or non-greasy basis. The basis may comprise hydrocarbons such as hard, soft or liquid paraffin, glycerol, beeswax, a metallic soap; a mucilage; an oil of natural origin such as coconut, almond, corn, arachis, castor or olive oil; wool fat or its derivatives, or a fatty acid such as stearic or oleic acid together with an alcohol such as propylene glycol or macrogols.

The extracts and/or compositions also may be impregnated into transdermal patches, plasters, and wound dressings such as bandages or hydrocolloid dressings, preferably in liquid or semi-liquid form. By way of example only, topically applied extracts and compositions in accordance with the present invention may be formulated into, or with, nail care products, face masks and scrubs, hair gels and mousses, hair tints, dyes and bleaches, products for waving, straightening and fixing hair, cleansing products such as shampoos, conditioning products such as lotions and creams, oils, shaving products such as creams and gels, skin washes, foams, bath and shower preparations such as oils and gels, moisturising products such as lotions, creams, gels and foams, anti-wrinkle products and anti-ageing products.

In particular circumstances, for example in the post surgical promotion of wound healing or the treatment of particular skin disorders, administration of compositions by injection, typically subcutaneous injection may be appropriate. Pharmaceutical forms suitable for injectable use include sterile aqueous solutions (where water soluble) or dispersions and sterile powders for the extemporaneous preparation of sterile injectable solutions. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of superfactants. The preventions of the action of microorganisms can be brought about by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilisation. Generally, dispersions are prepared by incorporating the various sterilised extract(s) into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the extract plus any additional desired extract from previously sterile-filtered solution thereof.

The present invention contemplates combination therapies, wherein extracts or compositions as described herein are coadministered with other suitable agents or treatments which may facilitate the desired therapeutic or cosmetic effect. For example, one may seek to aid wound healing with antibiotics, antimicrobial agents, or other wound healing agents in combination with extracts or compositions of the invention. By "coadministered" is meant simultaneous administration in the same formulation or in two different formulations via the same or different routes or sequential administration by the same or different routes. By "sequential" administration is meant a time difference of from seconds, minutes, hours or days between the administration of the two types of agents. The agents may be administered in any order.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

The present invention will now be described with reference to the following specific examples, which should not be construed as in any way limiting the scope of the invention.

EXAMPLES

Example 1

Preparation of a Combination Extract of *Vigna marina* (Burm.) Merr., *Cocos nucifera* L., *Terminalia catappa* L. and *Hibiscus tiliaceus* L. in Coconut Oil Coconut oil (200 mL) was added to fresh shredded leaves of *Vigna marina* (Burm.) Merr. (100 g) and fresh shredded leaves of *Terminalia catappa* L. (100 g). The mixture was placed in a crucible in a water bath at 100° C. for 20 min. The mixture was removed from the heat and immediately filtered and pressed to extract the coconut oil. The resultant coconut oil, containing extracts of *Vigna marina* (Burm.) Merr. and *Terminalia catappa* L., was added to the fresh crushed husk of a green nut of *Cocos nucifera* L. (100 g) and the shaved bark of *Hibiscus tiliaceus* L. (100 g). The mixture was left to settle for 4 h and then filtered and pressed to extract the coconut oil.

The coconut oil was then inverted and stored at less than 20° C. until the coconut oil solidified. Any remaining moisture or solid in the mixture were removed by decanting from the solidified coconut oil. The coconut oil was then heated in a hot water bath at approximately 56° C. and filtered. The resultant filtrate contained a combination extract of *Vigna marina* (Burm.) Merr., *Cocos nucifera* L., *Terminalia catappa* L. and *Hibiscus tiliaceus* L.

Example 2

Promotion of Wound Healing

A study was carried out to assess the wound healing capabilities of extracts of *Vigna marina* (Burm.) Merr., *Cocos nucifera* L., *Terminalia catappa* L. and *Hibiscus tiliaceus* L. prepared as described in Example 1. For the study 12 week old healthy female rats were used as an optimal healing model. Wounds were surgically created under anaesthesia and sterile conditions, and closed by primary intention (all tissues including the skin were closed with suture material) with intraoperative antibiotics and clean housing. A daily dose of 1 mL of the extract was applied topically to the surgical site. The extract was applied daily for as total of 10 days. The control animals received no treatment. At 3, 5, 7 and 10 days after creation of the site the wound histology was assessed and the wound tested for mechanical strength by distraction to failure testing.

The wound histology of the untreated wounds (control) and treated wounds (test) are shown in FIGS. 1A to 1H. The histology of the treated wounds show an early proliferation of the epithelium covering the wound in the first 3 days, followed by an infiltration of cells into the wound to commence regeneration and complete healing by day 7 with minimal evidence of wound by day 10. Evidence of wound healing was also observed in the untreated wounds by day 10 but this occurred at a slower rate than was observed in the treated wounds, thereby demonstrating that the extract enhances the rate of the natural healing process.

Figure 2A:
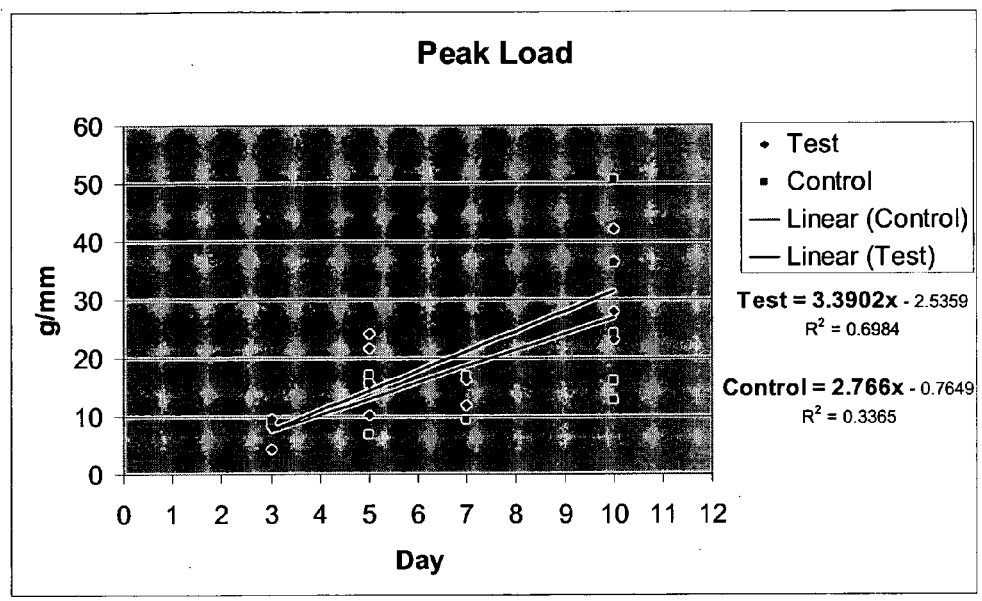
FIG. 2A shows the linear correlation and FIG. 2B is modelled into a non linear healing curve.
Figure 2B:
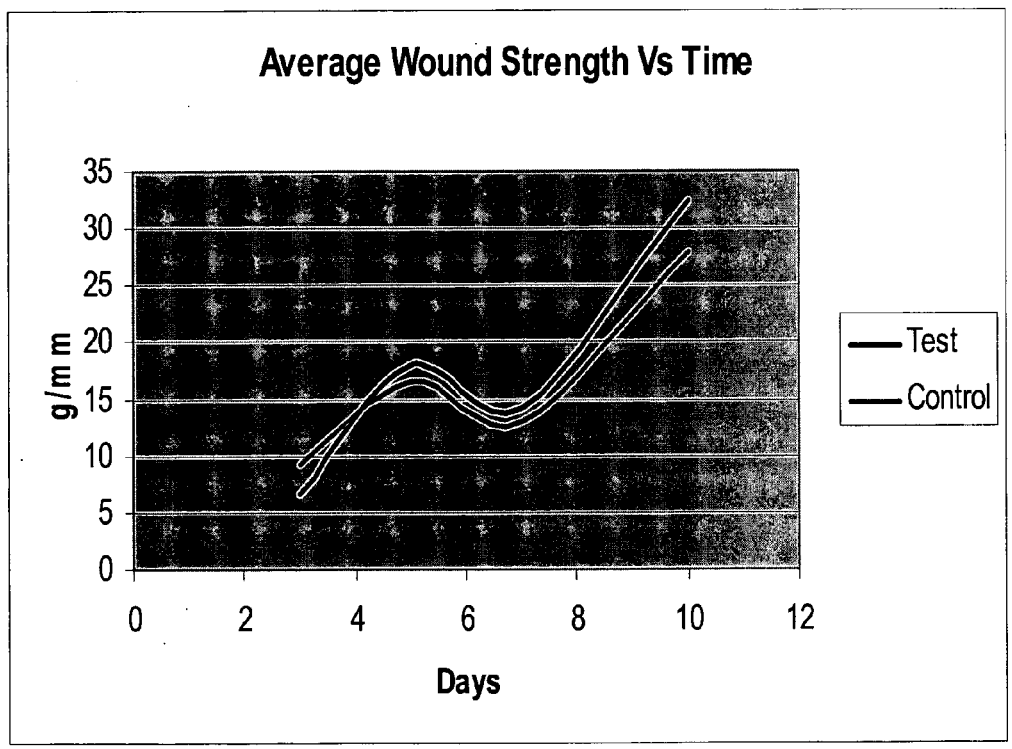

A graphical representation of the change in mechanical strength of the wound site during treatment is shown in FIG. 2A. The treated wound sites were found to have a 22% higher mechanical strength than the untreated wound sites. FIG. 2B shows that when the mechanical strength data was modelled into a non linear healing curve (to reflect healing pattern) the differences are preserved.

The results from the study show the that treatment of a wound with the combination extract of Example 1 both promotes wound healing and increases the mechanical strength of the skin at the wound site.

Example 3

Treatment of Oestrogen Deficient Skin

A study was carried out to assess the effect of an extract of *Vigna marina* (Burm.) Merr., *Cocos nucifera* L., *Terminalia catappa* L. and *Hibiscus tiliaceus* L. prepared as described in Example 1, on estrogen deficient skin. In the study a daily dose 1 mL of the extract was applied topically to the epithelial surface of the backs of 18 month old, oestrogen deficient (ovaries removed at age 6 weeks) rats (10 animals). The extract was applied daily for a total of 7 days. The control animals were 18 month old, oestrogen deficient (ovaries removed at age 6 weeks) rats with no topical application of the extract (10 animals). At 7 days the histology of the treated and control skin was assessed and the epithelial thickness determined.

The histological profile of treated and control skin from individual animals at 7 days is shown in FIGS. 3A to 3F. The histology of the treated skin compared to the control shows a thick highly cellular epithelium and a relative increase in cellularity of the collagen matrix.

Figure 4A:
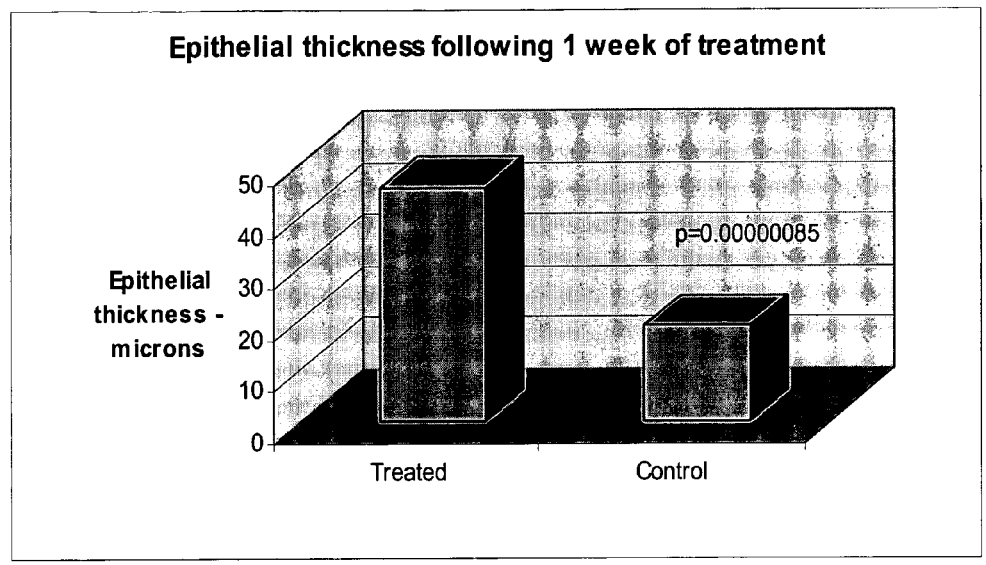
FIG. 4 shows the epithelial thickness of treated (daily application of a combination extract of *Vigna marina* (Burm.) Merr., *Cocos nucifera* L., *Terminalia catappa* L. and *Hibiscus tiliaceus* L. in coconut oil) and control (untreated) oestrogen deficient skin following 7 days of treatment (A) and oestrogen deficient skin adjacent to treatment area following 21 days of treatment (B).

A graphical representation of the epithelial thickness of the skin of treated and untreated animal is shown in FIG. 4A. An average increase of 145% in the epithelial thickness of the skin in treated compared to untreated animals was observed.

Figure 4B:
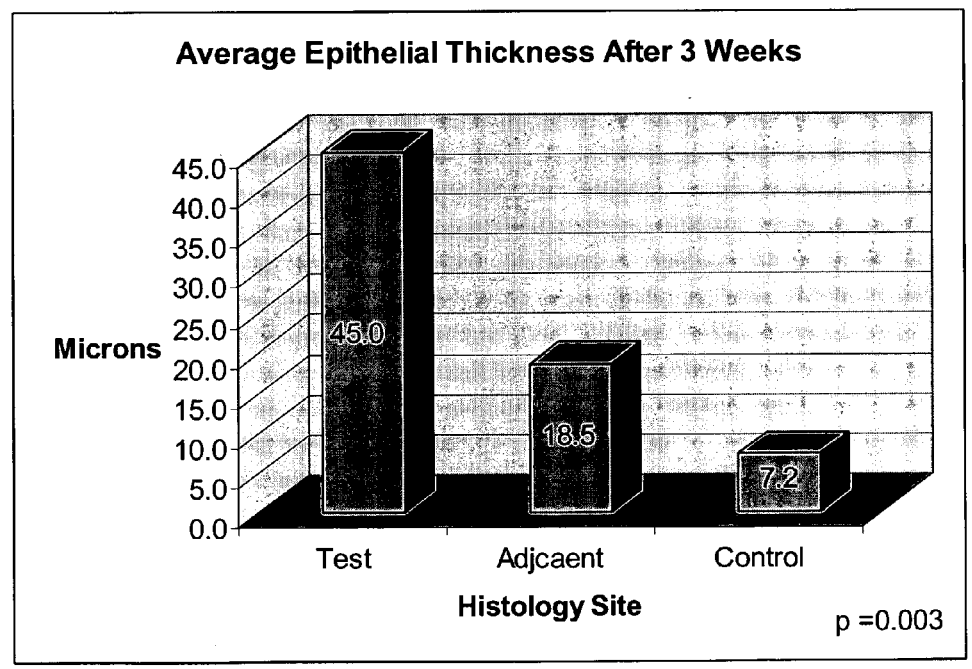

An identical study was carried out with the exception that the extract was applied daily for 3 weeks (10 animals). At 21 days the epithelial thickness of the treated skin (site of application and adjacent site) and untreated (control) skin was determined. This study demonstrates that the increase in epithelial thickness and cellularity of the collagen matrix observed over 7 days (see above) are maintained over 21 days of treatment. Epithelial thickness following 21 days of treatment is shown in FIG. 4B. The results in FIG. 4B show that the effect is not only seen in the area of application but also in the areas adjacent to the applied area implying that only a small dose is required to bring about the effects to aged oestrogen deficient skin.

Figure 5:
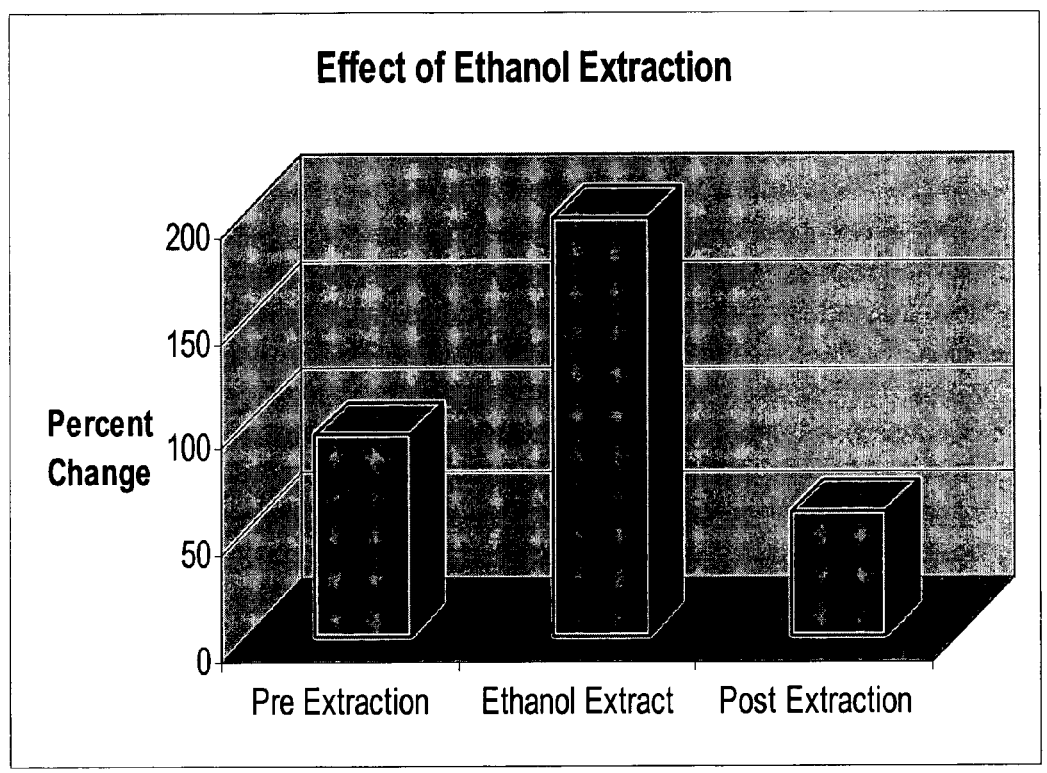
FIG. 5 shows the percentage change in epithelial thickness in oestrogen deficient skin following 7 days treatment comprising daily application of a combination extract of *Vigna marina* (Burm.) Merr., *Cocos nucifera* L., *Terminalia catappa* L. and *Hibiscus tiliaceus* L. Bar 1 (Pre-extraction), the extract is in coconut oil; Bar 2 (Ethanol extract), removal of coconut oil from the post-extraction extract; Bar 3 (Post extraction), the residual coconut oil fraction following ethanol extraction (Bar 2).

It was also demonstrated that the biological activity of the coconut oil based extract is soluble in ethanol. The extract in coconut oil (pre-extraction) was vigorously mixed 1:1 with ethanol for 5 min until the mixture was homogeneous and then left to stand for 5 min, the mixture was then frozen and the ethanol removed (ethanol extract) to leave coconut oil (post extraction) only. At 7 days the epithelial thickness was determined. FIG. 5 shows the percentage change in epithelial thickness of treated oestrogen deficient skin following the treatment. The results demonstrate that the activity of the extract is maintained when extracted into ethanol.

Example 4

Preparation of Extracts of *Vigna marina* (Burm.) Merr.

4.1: *Vigna Marina* (Burm.) Merr. Extract in Coconut Oil

The fresh crushed leaves, vine and bean of *Vigna marina* (Burm.) Merr. (100 g) were immersed in coconut oil (100 mL). The extract was prepared by cold pressing the *Vigna marina* (Burm.) Merr. and coconut oil mixture; or by heating the mixture. The cold pressing was carried out by placing the *Vigna marina* (Burm.) Merr. and coconut oil mixture inside a new coffee plunger and leaving the mixture to settle for 1 h, the plunger was then depressed thereby extracting the oil. The mixture was left to settle for a further 5 min and the plunger depressed again to release more oil. This process was repeated 5 times until no further oil was obtained. When the extract was prepared by heating, the *Vigna marina* (Burm.) Merr. and coconut oil mixture was heated in a crucible in a water bath at 100° C. for 20 min, removed from the heat, and then immediately filtered and pressed to extract the coconut oil. Any remaining moisture or solid in the extract after cold pressing or heating and filtering were removed by inverting the coconut oil extract and storing it at less than 20° C. until the coconut oil solidified and then decanting the solidified coconut oil; or by decanting in a separating funnel.

4.2: *Vigna Marina* (Burm.) Merr. Extract in Coconut Oil Following Extraction in Ethanol The fresh crushed leaves, vine and bean of *Vigna marina* (Burm.) Merr. (1000 g) were immersed in 95-100% ethanol (2000 mL) and left to steep for 24 h. The ethanol extraction of *Vigna marina* (Burm.) Merr. was agitated with coconut oil (250 mL). The coconut oil was decanted from the solution following standing for at least 2 h in a decanting vessel; or by the dilution of the ethanol solution from 95% to a lower concentration, nominally but not necessarily 50% ethanol and then decanted after settling of the layers. Any remaining moisture or solid in the mixture were removed by inverting the coconut oil extract and storing it at less than 20° C. until the coconut oil solidified and then decanting the solidified coconut oil; or by decanting in a separating funnel.

4.3 *Vigna Marina* (Burm.) Merr. Extract in Coconut Oil Following Extraction in Ethanol and Isopentane The fresh crushed leaves, vine and bean of *Vigna marina* (Burm.) Merr. (1000 g) were immersed in 95-100% ethanol (2000 mL) and left to steep for 6 h, the ethanol was then removed and the *Vigna marina* (Burm.) Merr. steeped in a second aliquot of ethanol (2000 mL) for a further 6 h.

The resultant ethanol was agitated with hexane, pentane, methyl butane or an equivalent hydrocarbon or fluoro/chloro/bromo-hydrocarbon (250 mL). The hydrocarbon was decanted from the solution following standing for at least 2 h in a decanting vessel; or by the dilution of the ethanol solution from 95% to a lower concentration, nominally but not necessarily 50% ethanol and then decanted after settling of the layers.

Coconut oil (250 mL) was added to the hydrocarbon solution and heated above the boiling point of the hydrocarbon (for example when hexane was used the solution was heated to 67° C.) to evaporate the hydrocarbon. 95% Ethanol (250 mL) was added to the hydrocarbon solution and heated above the boiling point of the hydrocarbon.

4.4: *Viva marina* (Burm.) Merr. Extract in Hydrocarbon Following Extraction in Ethanol The fresh crushed leaves, vine and bean of *Vigna marina* (Burm.) Merr. (1000 g) were immersed in 95-100% ethanol (2000 mL) and left to steep for 6 h, the ethanol was then removed and the *Vigna marina* (Burm.) Merr. steeped in a second aliquot of ethanol (2000 mL) for a further 6 h. The resultant ethanol solution was agitated with hexane, pentane, methyl butane or an equivalent hydrocarbon or fluoro/chloro/bromo-hydrocarbon (250 mL). The hydrocarbon was decanted from the solution following standing for at least 2 h in a decanting vessel; or by the dilution of the ethanol solution from 95% to a lower concentration, nominally but not necessarily 50% ethanol and then decanted after settling of the layers.

4.5: *Vigna Marina* (Burm.) Merr. Extract in Ethanol Following Extraction in Ethanol and Hydrocarbon The fresh crushed leaves, vine and bean of *Vigna marina* (Burm.) Merr. (1000 g) were immersed in 95-100% ethanol (2000 mL) and left to steep for 6 h, the ethanol was then removed and the *Vigna marina* (Burm.) Merr. steeped in a second aliquot of ethanol (2000 mL) for a further 6 h. The resultant ethanol solution was agitated with hexane, pentane, methyl butane or an equivalent hydrocarbon or fluoro/chloro/bromo-hydrocarbon (250 mL). The hydrocarbon was decanted from the solution following standing for at least 2 h. in a decanting vessel; or by the dilution of the ethanol solution from 95% to a lower concentration, nominally but not necessarily 50% ethanol and then decanted after settling of the layers. 95% Ethanol (250 mL) was added to the hydrocarbon solution and heated above the boiling point of the hydrocarbon (for example when hexane was used the solution was heated to 67° C.) to evaporate the hydrocarbon.

Example 5

Preparation of Extracts of *Cocos nucifera* L.

5.1: *Cocos Nucifera* L. Extract in Coconut Oil

The extract was prepared as described for *Vigna marina* (Burm.) in Example 4.1 with the exception that the fresh husk of the young nut of *Cocos nucifera* L. (100 g) was used.

5.2: *Cocos Nucifera* L. Extract in Coconut Oil Following Extraction in Ethanol

The extract was prepared as described for *Vigna marina* (Burm.) in Example 4.2 with the exception that the fresh husk of the young nut of *Cocos nucifera* L. (1000 g) was used.

5.3: *Cocos Nucifera* L. Extract in Coconut Oil Following Extraction in Ethanol and Hydrocarbon The extract was prepared as described for *Vigna marina* (Burm.) in Example 4.3 with the exception that the fresh husk of the young nut of *Cocos nucifera* L. (1000 g) was used.

5.4: *Cocos Nucifera* L. Extract in Hydrocarbon Following Extraction in Ethanol

The extract was prepared as described for *Vigna marina* (Burm.) in Example 4.4 with the exception that the fresh husk of the young nut of *Cocos nucifera* L. (1000 g) was used.

5.5: *Cocos Nucifera* L. Extract in Ethanol Following Extraction in Ethanol and Hydrocarbon The extract was prepared as described for *Vigna marina* (Burm.) in Example 4.5 with the exception that the fresh husk of the young nut of *Cocos nucifera* L. (100 g) was used.

Example 6

Preparation of Extracts of *Terminalia catappa* L.

6.1: *Terminalia catappa* L. Extract in Coconut Oil

The extract was prepared as described for *Vigna marina* (Burm.) in Example 4.1 with the exception that the fresh crushed leaves, vine and bean of *Terminalia catappa* L. (100 g) were used.

6.2: *Terminalia catappa* L. Extract in Coconut Oil Following Extraction in Ethanol The extract was prepared as described for *Vigna marina* (Burm.) in Example 4.2 with the exception that the fresh crushed leaves, vine and bean of *Terminalia catappa* L. (1000 g) were used.

6.3: *Terminalia catappa* L. Extract in Coconut Oil Following Extraction in Ethanol and Hydrocarbon The extract was prepared as described for *Vigna marina* (Burm.) in Example 4.3 with the exception that the fresh crushed leaves, vine and bean of *Terminalia catappa* L. (1000 g) were used.

6.4: *Terminalia catappa* L. Extract in Hydrocarbon Following Extraction in Ethanol The extract was prepared as described for *Vigna marina* (Burm.) in Example 4.4 with the exception that the fresh crushed leaves, vine and bean of *Terminalia catappa* L. (1000 g) were used.

6.5: *Terminalia catappa* L. Extract in Ethanol Following Extraction in Ethanol and Hydrocarbon The extract was prepared as described for *Vigna marina* (Burm.) in Example 4.5 with the exception that the fresh crushed leaves, vine and bean of *Terminalia catappa* L. (1000 g) were used.

Example 7

Preparation of Extract of *Hibiscus tiliaceus* L.

7.1: *Hibiscus tiliaceus* L. Extract in Coconut Oil

The extract was prepared as described for *Vigna marina* (Burm.) in Example 4.1 with the exception that the fresh crushed leaves, vine and bean of *Hibiscus tiliaceus* L. (100 g) were used.

Example 8

Effect of Individual Extracts of *Vigna marina* (Burm.) Merr. and *Terminalia catappa* L. on the Epithelial Thickness of Skin An assessment of the effect of each of the extracts (prepared as described in Examples 4 to 7) on the epithelial thickness of skin was carried out. A daily dose 1 mL of the extract was topically applied to the epithelial surface of the backs of 10 to 14 week old female rats for 7 days. A first control was treated with a daily dose 1 mL of coconut oil. A second control was the untreated surface of the backs of 10-14 week old female rats. At 7 days the histology of the treated and control skin was assessed.

Figure 6A:
FIG. 6 shows histologic profiles of skin of 10 to 14 weeks old rats following daily application for 7 days of A) no treatment; B) coconut oil; C) *Vigna marina* (Burm.) Merr. in coconut oil, D) *Vigna marina* (Burm.) Merr. in ethanol; E) *Vigna marina* (Burm.) Merr. in coconut oil following extraction with ethanol and isopentane; F) *Terminalia catappa* L. in coconut oil; G) *Terminalia catappa* L. in ethanol; H) *Terminalia catappa* L. in hydrocarbon following ethanol extraction; I) *Terminalia catappa* L. in coconut oil following extraction with ethanol and hydrocarbon; and J) *Terminalia catappa* L. in coconut oil following extraction with ethanol and hydrocarbon. The skin samples were stained with hematoxylin and eosin and are shown at ×400 magnification.
Figure 6B:
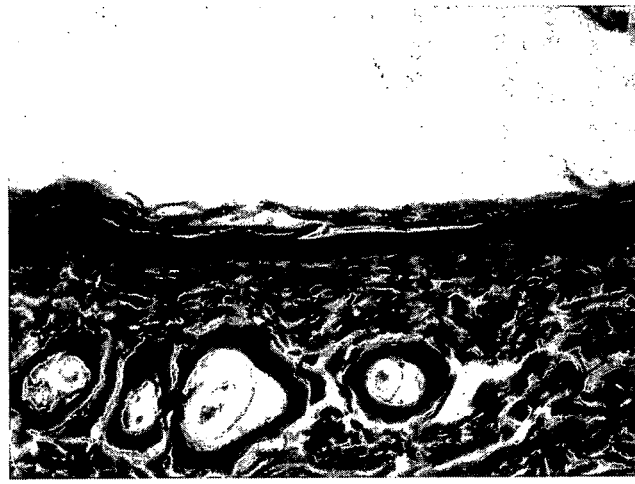

FIGS. 6A to 6J show the histology of the treated and control skin. The results show that coconut oil alone (FIG. 6B) has no obvious effect on the histological profile of the skin. The histology of skin treated with coconut oil alone is comparable to untreated skin (FIG. 6A).

Figure 6C:
Figure 6D:
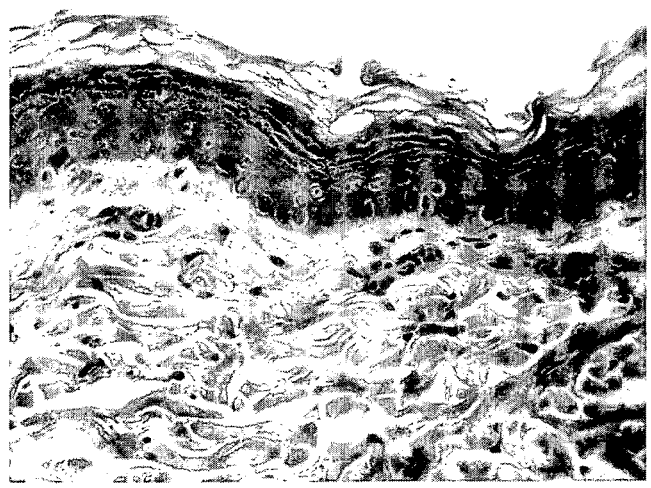
Figure 6E:
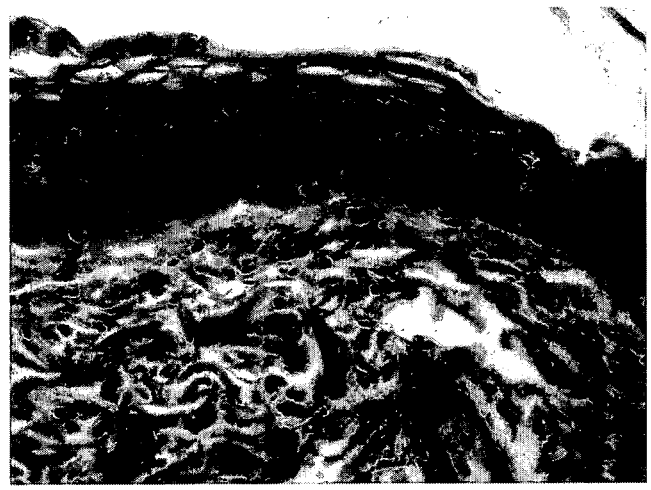
Figure 6F:
Figure 6G:
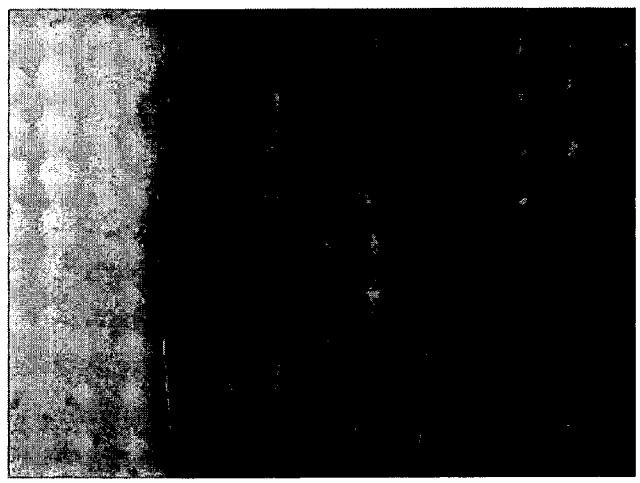
Figure 6H:
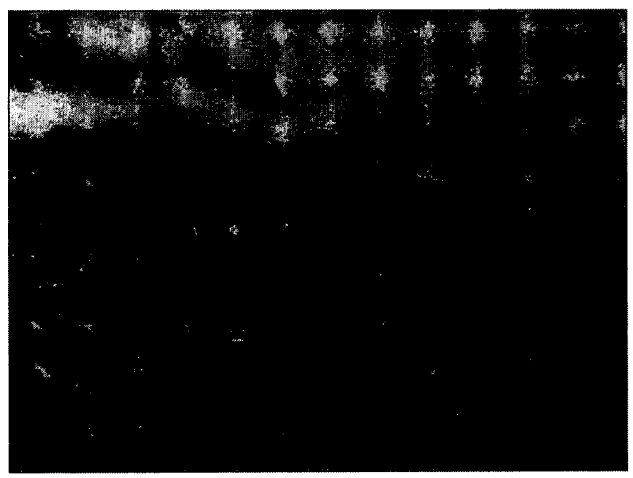
Figure 6I:

FIGS. 6C to 6E show the histology after a daily application of an extract of *Vigna marina* (Burm.) Merr. in coconut oil (FIG. 6C); in ethanol (FIG. 6D); and in coconut oil following extraction with ethanol and hydrocarbon (FIG. 6E). The results show a marked change in epithelial cell thickness. Furthermore, there is evidence of vascular structures in the dermis and no inflammatory infiltrate. In summary, the effect of *Vigna marina* (Burm.) Merr. on the skin was observed in all extraction solutions, indicating the ability to concentrate the extract in alcohol, and hydrocarbon extractions.

Figure 6J:
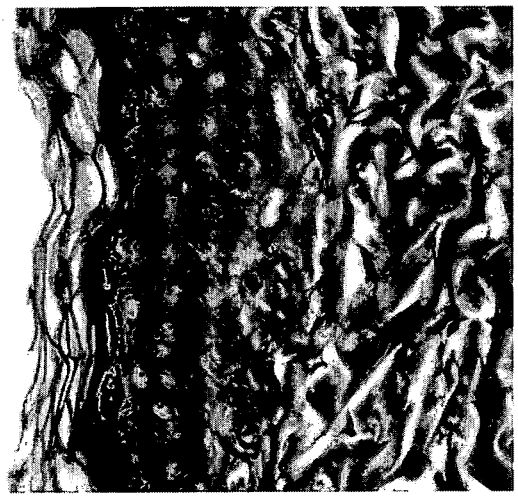

FIGS. 6F to 6J show the histology after a daily application of an extract preparation of *Terminalia catappa* L. in coconut oil (FIG. 6F); in hydrocarbon (FIG. 6G); in ethanol (FIG. 6H); coconut oil following extraction with ethanol (FIG. 6I); and coconut oil following extraction with ethanol and hydrocarbon (FIG. 6J). The histological profiles show that the extracts have limited activity in the ethanol or hydrocarbon extract alone, but that activity is maintained if *Terminalia catappa* L. is extracted directly into coconut oil, or into ethanol or hydrocarbon and then extracted into coconut oil.

Example 9

Effect of Individual and Combination Extracts of *Vigna marina* (Burm.) Merr., *Cocos nucifera* L., *Terminalia catappa* L. and *Hibiscus tiliaceus* L. on the Epithelial Thickness of Skin An assessment of the activity of each of the extracts prepared as described in Examples 4.1, 5.1, 6.1 and 7.1 was carried out. A daily dose of 1 mL of *Vigna marina* (Burm.) Merr. extract in coconut oil (Example 4.1); *Cocos nucifera* L. extract in coconut oil (Example 5.1); 1 mL of *Terminalia catappa* L. extract in coconut oil (Example 6.1); and/or 1 mL of *Hibiscus tiliaceus* L extract in coconut oil (Example 7.1) was administered topically. Each extract was applied alone or in combination with a second extract, for example 0.5 mL *Vigna marina* (Burm.) Merr. extract in coconut oil+0.5 mL *Cocos nucifera* L. extract in coconut oil to give a dose of 1 mL. The extracts were applied topically to the epithelial surface of the backs of 10-14 week old female rats. At 7 days the epithelial thickness of the skin was determined.

Figure 7A:
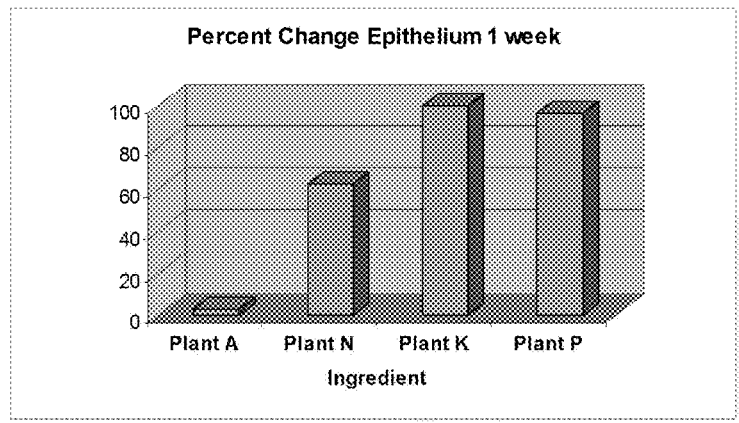
FIG. 7 shows the percent change in epithelial thickness of skin of 10 to 14 weeks old rats following 7 days of treatment with A) *Vigna marina* (Burm.) Merr. extract in coconut oil (Plant P); *Cocos nucifera* L. extract in coconut oil (Plant N); *Terminalia catappa* L. extract in coconut oil (Plant N); and *Hibiscus tiliaceus* L. in coconut oil (Plant A) and B) pairwise combination of the aforementioned extracts.
Figure 7B:
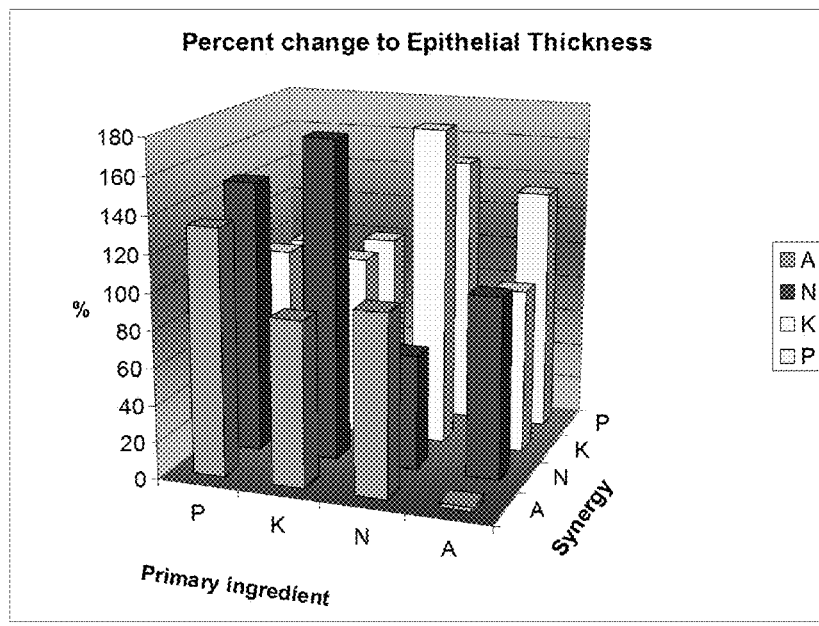
Figure 8A:
FIG. 8 shows histologic differences in skin of 10 to 14 weeks old rats treated with an extract of *Vigna marina* (Burm.) Merr., *Cocos nucifera* L. and *Terminalia catappa* L. in coconut oil (100%) prepared as described in Example 10, at concentrations of A) 0%; B) 1%; C) 5%; D) 10%; E) 50%; and F) 100%. The skin samples were stained with hematoxylin and eosin and are shown at ×400 magnification.
Figure 8B:
Figure 8C:
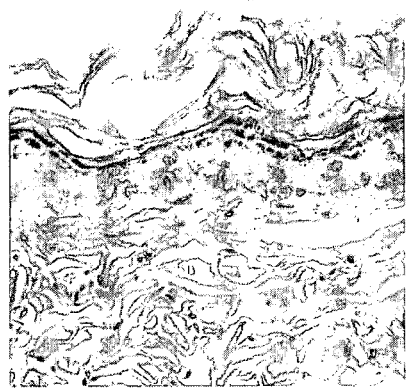
Figure 8D:
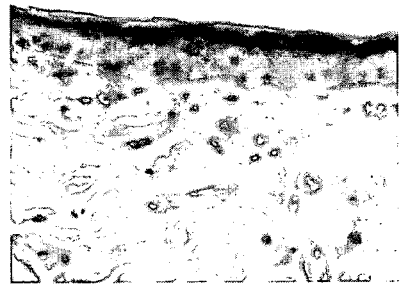
Figure 8E:
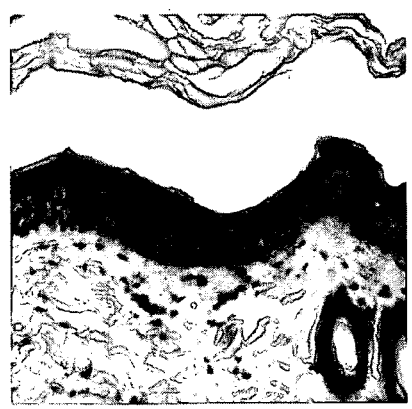
Figure 8F:

FIGS. 7B and 7B show the percentage change in the epithelium thickness at 7 days compared to control untreated skin on the same animal. FIG. 7A shows that topical application of *Vigna marina* (Burm.) Merr. extract in coconut oil and *Terminalia catappa* L. extract in coconut oil cause the largest increase in epithelium thickness over a 7 day period when the extract is applied alone. FIG. 7B details the percent change in epithelial thickness when each extract is applied in combination with one other extract. The results show that *Cocos nucifera* L. extract has a synergistic effect with both *Vigna marina* (Burm.) Merr. extract and *Terminalia catappa* L. extract and that *Hibiscus tiliaceus* L. has a synergistic effect with *Vigna* marina (Burm.) Merr.

A further assessment (data not shown) using each of the extracts prepared as described in Examples 4 to 7 was carried out and confirmed the results shown in FIGS. 6A to 6J and 7A and 7B. The assessment utilised 303 female Sprague Dawley rats and 34 New Zealand white rabbits. The extracts were applied topically to the epithelial surface of the backs of 18 month old ovarectomized and sham ovarectomized rats, and 12 week old rats for up to 21 days and to the skin of 12 week old New Zealand white rabbits for 7 days.

In a parallel study a moisturiser (hydroderm), the topical antibiotic Chloromycetin (chloramphenicol), coconut oil, or coconut oil extracted into ethanol were applied to the epithelial surface of the backs of 18 month old ovarectomized and sham ovarectomized rats and compared to the epithelial surface of an adjacent untreated site. No significant difference was recorded between the thickness of the treated skin compared to the untreated adjacent skin for animals treated with hydroderm, Chloromycetin (chloramphenicol), coconut oil, or coconut oil extracted into ethanol. The results indicate that the changes noted in the epithelium are due to the application of the extracts and are not related to moisturising effects of, for example, coconut oil in the extracts. The results also indicate that the changes noted in the epithelium are not related to any antimicrobial capacity of the extracts as the changes are not able to be replicated by chloramphenicol.

All the animals tolerated the treatment well. There were no deaths or illness associated with the topical treatments. The region of skin applied did not appear inflamed macroscopically or microscopically in any active treatments. Histological changes to the epithelium in the region of application of the extracts were noted. The difference between the regions of application and control regions revealed a change to the epithelial structure with hypertrophy of many layers of the epithelium and an increase in the stratified appearance. The increase in epithelium thickness was over 100% and was both reproducible and statistically quantifiable.

The effect seen on the epithelium of the skin to which the extracts were applied was the same in young animals as it was in both aged animals and aged oestrogen deficient animals. This is despite the differences in the baseline histology of the untreated animals in each of these groups. The effect of the extracts on the skin of rabbits was similar to that seen in the rats with similar changes noted to the epithelium and the epithelial structures such as hair follicles.

Example 10

Preparation of Combination Extract of *Vigna marina* (Burm.) Merr., *Cocos nucifera* L., and *Terminalia catappa* L The fresh crushed leaves, vine and bean of *Vigna marina* (Burm.) Merr. (2.5 kg), fresh husk of the young nut of *Cocos nucifera* L. (2.5 kg) and fresh crushed leaves, vine and bean of *Terminalia catappa* L (1 kg) were mulched separately.

*Vigna marina* (Burm.) Merr. was added to 95% ethanol (5 L) and agitated and the mixture allowed to sit for 12 h. The mulched material of *Vigna marina* (Burm.) Merr. was removed and added to a second vat of 95% ethanol (5 L) and the mixture allowed to sit for 12 h. The first 5 L of ethanol added to a large vat.

The mulched material of *Vigna marina* (Burm.) was removed from the second aliquot of ethanol and added to a third aliquot of 95% ethanol (5 L). The mulched material of *Cocos nucifera* L. was added to the second vessel of 95% ethanol (5 L) and allowed to stand for 12 h. The mulched material of *Vigna marina* (Burm.) (now almost colourless) was removed from the third aliquot of 95% ethanol and discarded. The mulched material of *Cocos nucifera* L. was removed from the second vessel and placed in the third aliquot of 95% ethanol. The third aliquot was allowed to stand for 12 h. The second aliquot of 95% ethanol was added to the first aliquot.

The mulched material of *Cocos nucifera* L. was removed from the third aliquot of 95% ethanol and placed into a fourth aliquot of 95% ethanol (5 L). The mulched material of *Terminalia catappa* L was added to third aliquot of 95% ethanol. Both the third and fourth aliquots were allowed to stand for 12 h.

The mulched material of *Cocos nucifera* L. was removed from the fourth aliquot and discarded. The mulched material of *Terminalia catappa* L was removed from the third aliquot of 95% ethanol and placed in the fourth aliquot of 95% ethanol and allowed to stand for 12 h. The third aliquot of 95% ethanol was added to the first and second aliquots.

The mulched material of *Terminalia catappa* L was removed from the fourth aliquot, added to a fifth aliquot of 95% ethanol (5 L) 95% ethanol and allowed to stand for 12 h. The mulched material of *Terminalia catappa* L (now colourless) was removed from the fifth aliquot. Both the fourth and fifth aliquots of 95% ethanol were added to the first three aliquots. To the resultant extracted mixture virgin coconut oil (1 L) was added. The mixture was mixed vigorously for 5 min every 15 min for a period of 4 h. The mixture was then heated to boiling and held at greater than 80° C. until the volume of the mixture was reduced from 26 L to 3 L. The resultant mixture was allowed to cool and settle. The coconut oil was decanted from the top of the mixture and placed in sealable vessels inverted in a refrigerator. The coconut oil was allowed to solidify and the remaining aqueous components removed and discarded. The coconut oil was then heated in a hot water bath at approximately 56° C. and filtered.

Example 11

Figure 9A:
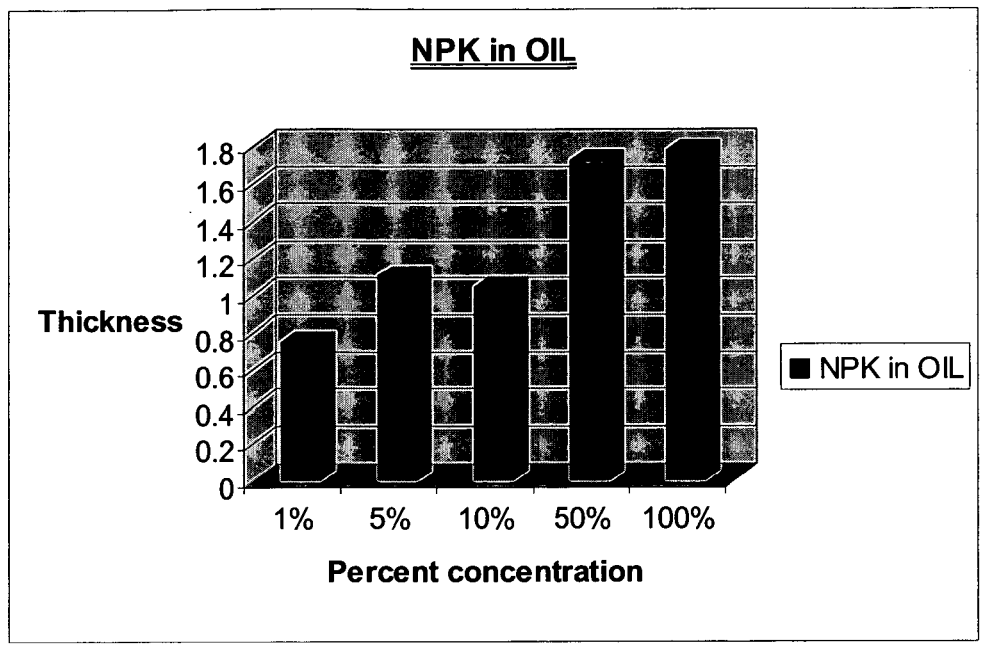
FIG. 9 shows the epithelial thickness (A) and percent change in epithelial thickness (B) of skin of 10 to 14 weeks old rats treated with a daily application of a combination extract of *Vigna marina* (Burm.) Merr., *Cocos nucifera* L. and *Terminalia catappa* L. in coconut oil (NPK in oil) prepared as described in Example 10, at concentrations of 0%, 1%; 5%; 10%, 50%, 100%.
Figure 9B:
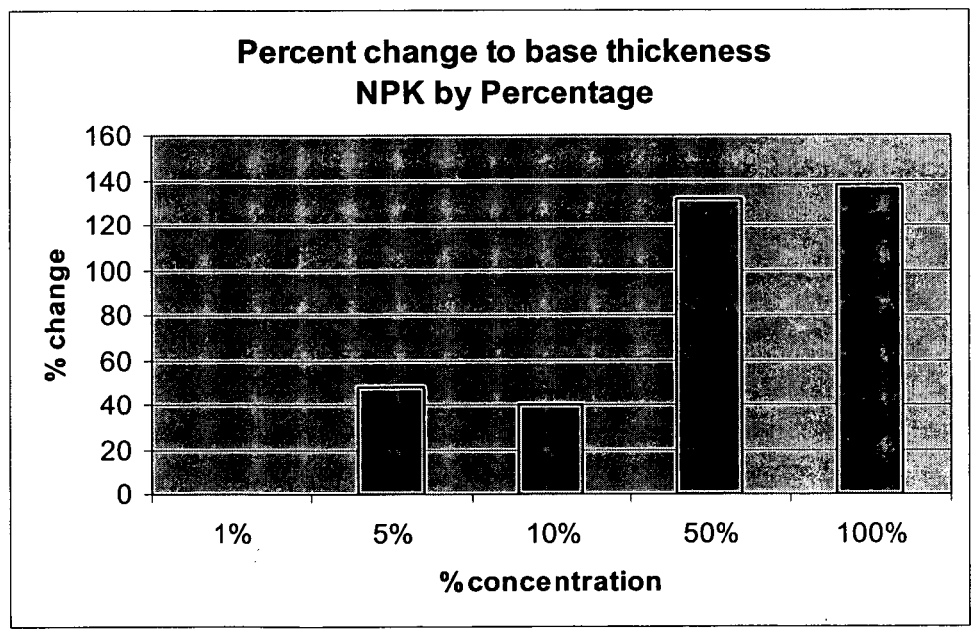
Figure 10A:
FIG. 10 shows the histology of skin treated with an extract of *Vigna marina* (Burm.) Merr., *Cocos nucifera* L. and *Terminalia catappa* L. in coconut oil at A) 30% in chlorhexidine; B) 5% in hydroderm moisturiser; C) 25% in chloramphenicol solution; D) 50% in chloramphenicol ointment; and E) 0% in chloramphenicol ointment.
Figure 10B:
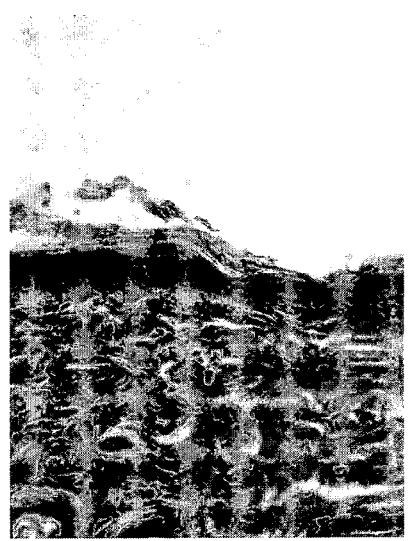
Figure 10C:
Figure 10D:
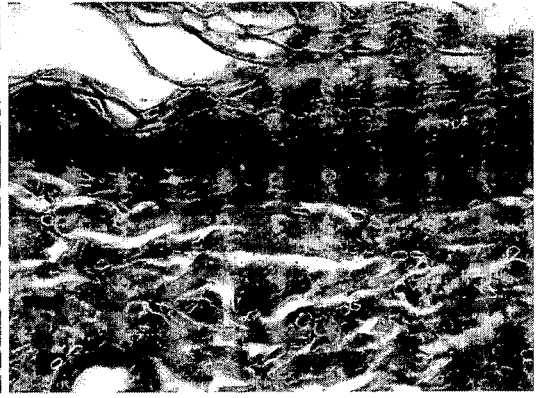
Figure 10E:

Dose Dependence of Combination Extract of *Vigna marina* (Burm.) Merr., *Cocos nucifera* L., and *Terminalia catappa* L To assess the dose dependence of the combination extract prepared as described in Example 10, a daily dose 1 mL of the extract of was topically applied to the epithelial surface of the backs of 10-14 week old female rats. The concentration of the extract was 100%. The extract was also applied at 50%, 10%, 5% and 1%. These extracts were prepared by dilution of the 100% extract with coconut oil. The skin was treated with a daily topical application for 7 days. The control animals were untreated 10-14 week old female rats. FIGS. 8A to 8F show the histology of the skin at 7 days. The results demonstrate the dose dependent relationship of the extract with the epithelial thickest and the cellularity more apparent after a daily application of 50% or 100% of the extract. FIGS. 9A and 9B shows the epithelial thickness and percent change in epithelial thickness of the skin at 7 days. An increase of over 130% in the epithelial thickness of the skin was observed for animals treated with 50% or 100% of the combination extract.

Example 12

Effect of Combination Extract of *Vigna marina* (Burm.) Merr., *Cocos nucifera* L., and *Terminalia catappa* L in Admixtures The extract of *Vigna marina* (Burm.) Merr., *Cocos nucifera* L. and *Terminalia catappa* L. in coconut oil (100%) prepared as described in Example 10, was admixed with chlorhexidine; hydroderm moisturiser; 25% Chloramphenicol and 50% Chloramphenicol. Each mixture was applied (1 mL) topically to the epithelial surface of the backs of 10-14 week old female rats for 7 days. At 7 days the histology of the treated skin was assessed.

The histological profiles are shown in FIGS. 10A to 10E and show that the efficacy of the extract is not attenuated by the presence of commercial ointments or solutions and that the extract is compatible with antiseptic and antibiotic applications.

The invention claimed is:

1. A method of treating a surgical or non-surgical wound in a subject in need thereof, the method comprising topically applying to affected skin of the subject a biologically active composition comprising an effective amount of: (i) a coconut oil extract of *Cocos nucifera* L. husk and (ii) a coconut oil extract of at least one plant material selected from the group consisting of a leaf, vine or bean of *Vigna marina* (Burm.) Merr. and a leaf, vine or bean of *Terminalia catappa* L., wherein (i) and (ii) are obtained by extracting the *Cocos nucifera* L. husk and the at least one plant material in coconut oil.

2. The method of claim 1, wherein the non-surgical wound is a burn, graze, cut or abrasion.

3. The method of claim 1, wherein the composition is applied to the affected skin daily for at least one week.

4. The method of claim 3, wherein the composition is applied in an amount of 0.0001 mg to 1,000 mg per kg body weight of the subject per day.

5. The method of claim 3, wherein the composition is applied in an amount of 0.1 mg to 1.0 mg per kg body weight of the subject per day.

6. The method of claim 3, wherein the composition is applied in an amount of 5.0 mg to 15 mg per kg body weight of the subject per day.

* * * * *